(12) United States Patent
Johansson et al.

(10) Patent No.: US 11,443,847 B2
(45) Date of Patent: Sep. 13, 2022

(54) ANALYZING EFFICIENCY BY EXTRACTING GRANULAR TIMING INFORMATION

(71) Applicant: KONINKLIJKE PHILIPS N.V., Eindhoven (NL)

(72) Inventors: Henrik Johansson, Foster City, CA (US); Ram Balasubramanian, Foster City, CA (US); Anand Mohan Tumuluri, Foster City, CA (US); Yogesh Pandit, Foster City, CA (US); Ashish Patel, Foster City, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 828 days.

(21) Appl. No.: 15/528,778

(22) PCT Filed: Nov. 25, 2015

(86) PCT No.: PCT/IB2015/059113
§ 371 (c)(1),
(2) Date: May 23, 2017

(87) PCT Pub. No.: WO2016/084010
PCT Pub. Date: Jun. 2, 2016

(65) Prior Publication Data
US 2017/0323054 A1 Nov. 9, 2017

Related U.S. Application Data

(60) Provisional application No. 62/084,604, filed on Nov. 26, 2014.

(51) Int. Cl.
*G16H 40/20* (2018.01)
*G16H 30/20* (2018.01)
(Continued)

(52) U.S. Cl.
CPC ............. *G16H 40/20* (2018.01); *A61B 5/055* (2013.01); *A61B 5/7221* (2013.01); *A61B 6/032* (2013.01);
(Continued)

(58) Field of Classification Search
None
See application file for complete search history.

(56) References Cited

U.S. PATENT DOCUMENTS 6,689,055 B1   2/2004  Mullen et al.
9,020,849 B2   4/2015  Kasai et al.
(Continued)

FOREIGN PATENT DOCUMENTS

AU      2012261569 A1    1/2013
JP      2010051476       3/2010
WO      WO-2011124922 A1 * 10/2011 ............... G09B 9/00

*Primary Examiner* — Evangeline Barr
*Assistant Examiner* — Jordan L Jackson

(57) ABSTRACT

A system and method determines efficiency data of a technician performing a Medical Data Acquisition Procedure (MDAP), using a Medical Data Acquisition System (MDAS). The method includes receiving timing data including Digital Imaging and Communications in Medicine (DICOM) metadata obtained during the MDAP by the MDAS. The DICOM metadata includes time duration information relating to each of a plurality of stages of the MDAP. The method includes determining the efficiency data of the technician as a function of the timing data and predetermined efficiency data defined for the MDAP using the MDAS.

15 Claims, 12 Drawing Sheets

(51) Int. Cl.
  *A61B 5/055* (2006.01)
  *A61B 5/00* (2006.01)
  *A61B 6/03* (2006.01)
  *A61B 6/00* (2006.01)
  *A61B 8/08* (2006.01)
  *A61B 8/00* (2006.01)

(52) U.S. Cl.
  CPC .............. *A61B 6/563* (2013.01); *A61B 6/581* (2013.01); *A61B 8/0883* (2013.01); *A61B 8/481* (2013.01); *A61B 8/565* (2013.01); *A61B 8/582* (2013.01); *G16H 30/20* (2018.01)

(56) References Cited

U.S. PATENT DOCUMENTS

| | | | |
|---|---|---|---|
| 2004/0267575 | A1 | 12/2004 | Boing |
| 2010/0070327 | A1* | 3/2010 | Chua .................... G06Q 10/109 705/2 |
| 2010/0179428 | A1* | 7/2010 | Pedersen ................. A61B 8/00 600/443 |
| 2013/0093829 | A1 | 4/2013 | Rosenblatt et al. |
| 2014/0004488 | A1* | 1/2014 | Tepper ................. G09B 23/286 434/219 |
| 2014/0204190 | A1 | 7/2014 | Rosenblatt, III |
| 2016/0124949 | A1* | 5/2016 | Chau .................... G06F 19/321 707/665 |
| 2016/0328998 | A1* | 11/2016 | Pedersen .............. A61B 8/4254 |

\* cited by examiner

Timeline Information
550

Procedure Timing Information
700

Table Fraction Timing Information
750

Activity Map 900

ANALYZING EFFICIENCY BY EXTRACTING GRANULAR TIMING INFORMATION

Cross-Reference to Prior Applications

This application is the U.S. National Phase application under 35 U.S.C. § 371 of International Application No. PCT/IB2015/059113, filed on Nov. 25, 2015, which claims the benefit of U.S. Provisional Application No. 62/084,604, filed on Nov. 26, 2014. This application is hereby incorporated by reference herein.

A medical institution may have a plurality of Medical Data Acquisition Systems (MDAS) configured to generate medical data corresponding to various medical procedures. For example, the MDAS may be an imaging device used to visualize internal structures of a body. For example, the imaging device may be a Magnetic Resonance Imaging (MRI) device. The data gathered from using this technique may provide a basis in which an anatomical image may be generated. Specifically, a cross sectional, axial image of internal structures of the body may be represented in a two-dimensional image or more complex images may be generated as a three-dimensional image. In this manner, a non-invasive modality for imaging soft tissue is provided. The image may be used by a user such as a physician, technician, etc. to determine whether the internal structures captured in the image are healthy, injured, etc. from determining whether any anomalies are present.

Systems have been provided to analyze whether the imaging procedure is properly performed and the images generated therefrom are correctly represented. Further systems have been provided to analyze administrative aspects of the procedures performed using the MDASs. Specifically, radiology analytics applications provide an overview of operations within a radiology department based on clinical, financial, and operational data extracted from a variety of information systems and feeds. For example, components may include scorecards, dashboards, and reports based on performance indicators such as exam volume, turnaround times, relative value units (RVU), etc. The applications may give insight into and allow for improvement of productivity, workflow, resource utilization, patient experience, and quality of care. The use cases may be driven by a variety of reasons such as legislative and regulatory requirements, quality of care, reimbursement models, profitability, etc. The applications may generate the information based upon different sources including event information from a HL7 feed including a start time and an end time of a procedure. However, those skilled in the art will understand that procedures include a plurality of substeps and information regarding simply an overall time frame may be insufficient to provide the necessary information to generate efficiency information.

Accordingly, it is desirable to determine timing information of a procedure including substeps for a procedure performed by a technician using a MDAS to further generate efficiency information.

The exemplary embodiments are directed to a method for determining efficiency data of a technician performing a Medical Data Acquisition Procedure (MDAP), using a Medical Data Acquisition System (MDAS), comprising: receiving timing data including Digital Imaging and Communications in Medicine (DICOM) metadata obtained during the MDAP by the MDAS, the DICOM metadata including time duration information relating to each of a plurality of stages of the MDAP; and determining the efficiency data of the technician as a function of the timing data and predetermined efficiency data defined for the MDAP using the MDAS.

The exemplary embodiments are directed to a method for scheduling patients for one of a plurality of Medical Data Acquisition Procedures (MDAP), using a Medical Data Acquisition System (MDAS), comprising: receiving first user data including first Digital Imaging and Communications in Medicine (DICOM) metadata obtained during at least one prior performance of the MDAPs using the MDAS by a first technician, the DICOM metadata including time duration information relating to each of a plurality of stages of the MDAP; receiving at least one second user data including second DICOM metadata obtained during at least one prior performance of the MDAPs using the MDAS by a respective second technician; determining performance data for the first user and the at least one second user as a function of the first user data, the second user data, a type of the MDAS, and a type of the MDAPs; and determining a schedule for the patients to have the MDAP performed using the MDAS based upon the performance data.

The exemplary embodiments are directed to a method for determining performance data of a plurality of Medical Data Acquisition Systems (MDAS) performing a Medical Data Acquisition Procedure (MDAP), comprising: receiving first timing data including first Digital Imaging and Communications in Medicine (DICOM) metadata obtained during the MDAP by a first one of the MDAS, the DICOM metadata including time duration information relating to each of a plurality of stages of the MDAP from using the first MDAS; receiving second timing data including second DICOM metadata obtained during the MDAP by a second one of the MDAS, the DICOM metadata including time duration information relating to each of the stages of the MDAP from using the second MDAS; and determining the performance data for each of the first and second MDAS based upon the first and second timing data.

Figure 1:
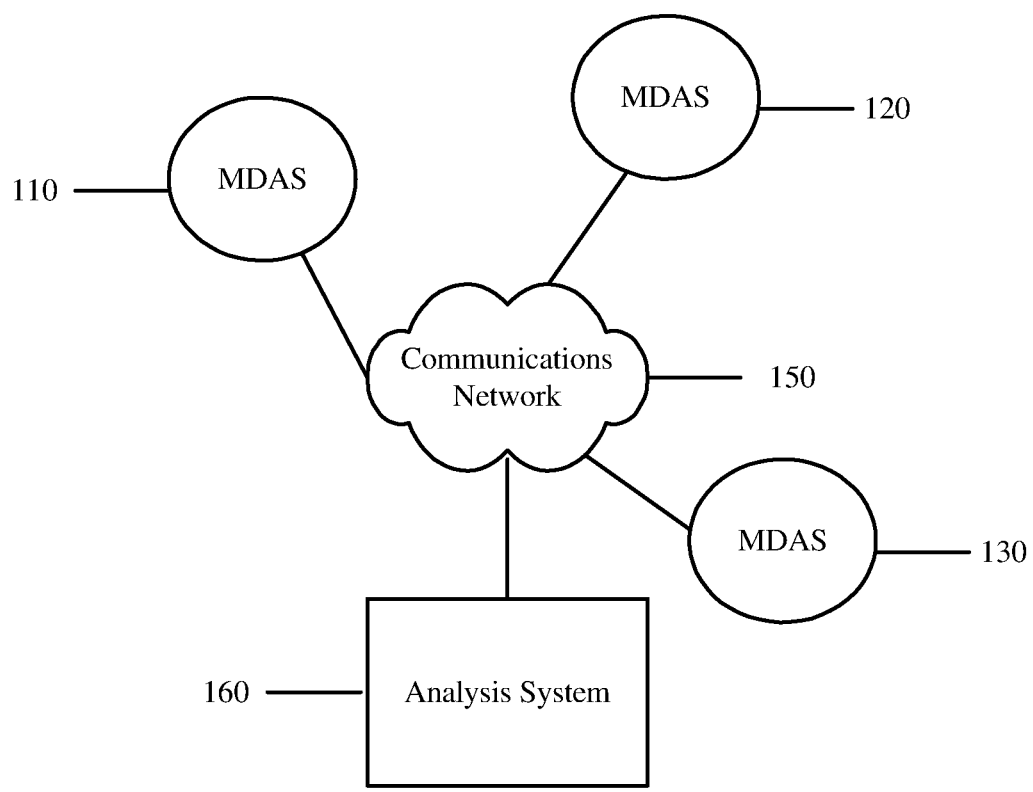
FIG. 1 shows a health care service system according to the exemplary embodiments.

The exemplary embodiments may be further understood with reference to the following description of the exemplary embodiments and the related appended drawings, wherein like elements are provided with the same reference numerals. The exemplary embodiments are related to a system and method of generating efficiency information of technicians or operators, determining a schedule for procedures to be performed, and determining performance information of devices performing procedures. Specifically, Digital Imaging and Communications in Medicine (DICOM) metadata may be used as a basis to generate timing information for the procedures performed using at least one Medical Data Acquisition System (MDAS). The DICOM metadata may particularly provide timing information regarding substeps of the procedures being performed. The efficiency information, the schedule, the performance information, the technicians, the procedures, the MDAS, the DICOM metadata, and related methods will be explained in further detail below.

The exemplary embodiments are described herein with regard to technicians and devices related to a medical field. Specifically, the technicians may utilize the MDAS in performing the corresponding medical or imaging procedure. However, it should be noted that the relation to the medical field is only exemplary. Those skilled in the art will understand that the exemplary embodiments and its determination of the efficiency information may be applicable to any number of fields utilizing corresponding devices performing various procedures by users such as technicians.

FIG. 1 shows a health care service system 100 according to exemplary embodiments. One of the services of the health care service system 100 is to acquire medical data relating to a patient. For example, the patient may have a medical procedure such as an imaging scan to be performed on a specific body portion. The system 100 may include a plurality of MDASs 110, 120, 130, a communications network 150, and an analysis system 160.

The MDASs 110, 120, 130 may be utilized to perform a medical data acquisition procedure (MDAP) to generate the medical data of the patient. The MDAP may range from any number of different procedures used in gathering the medical data such as magnetic resonance imaging, echocardiography, computed tomography, etc. each of which may be done at different body portions. As those skilled in the art will understand, other data may also be generated during the MDAP. It should be noted that any number of MDASs may be included in the system and that the use of three MDASs 110, 120, 130 is only exemplary.

The MDASs 110, 120, 130 may be embodied in a procedure area within a hospital, institution, department, etc. The procedure area may include a plurality of components such as a patient table where the patient lies or is positioned during the MDAP, a corresponding procedure device such as a MRI machine including a bore in which the patient table retracts thereinto, an imaging device that receives information from the procedure device to generate images to be viewed by the technician, etc.

Figure 2:
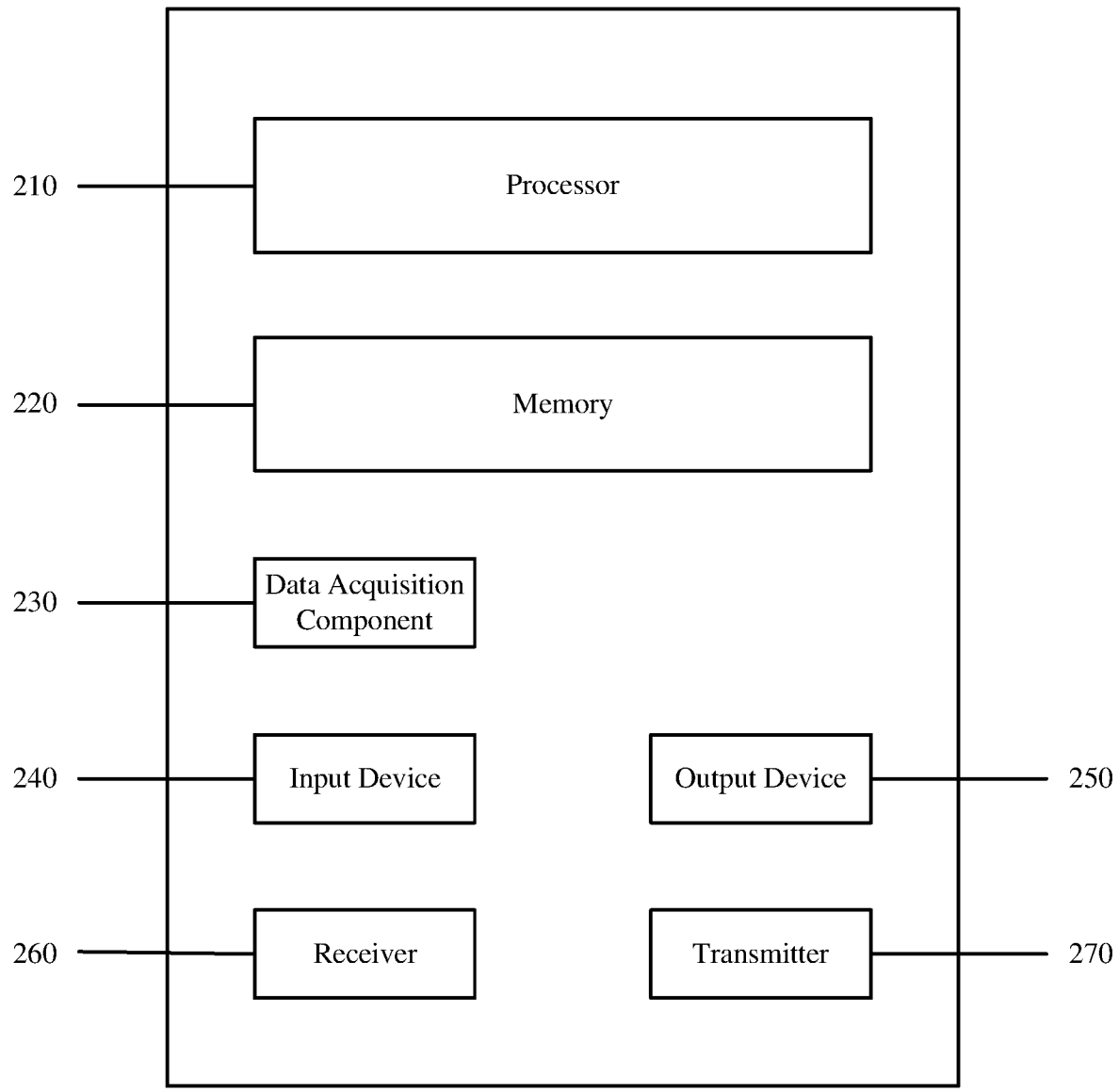
FIG. 2 shows the medical data acquisition system of FIG. 1 according to the exemplary embodiments.

FIG. 2 shows the MDAS 110 according to exemplary embodiments. The MDAS 110 may also represent a general description for the MDAS 110, 120, 130. However, it should again be noted that the MDAS 110 may be for any type of MDAP. Therefore, the components described herein are exemplary only and the MDAS 110 may include further components to properly perform the MDAP. The MDAS 110 may include a processor 210, a memory 220, a data acquisition component 230, an input device 240, an output device 250, a receiver 260, and a transmitter 270.

The data acquisition component 230 may be a component which generates the medical data of the patient. The data acquisition component 230 may include, for example, a Magnetic Resonance Imaging (MRI) machine, a computed topography (CT) machine, an ultrasound machine, an X-Ray machine, a Nuclear Magnetic Resonance (NMR) Machine, etc. Accordingly, the data acquisition component 230 may include corresponding subcomponents such as coils for the MRI machine, a probe generating ultrasounds for the ultrasound machine, etc.

The processor 210 may include an application to perform the MDAP using the data acquisition component 230 as well as utilize other components of the MDAS 110. The memory 220 may store the generated medical data along with other information used in subsequent processing. Specifically, according to the exemplary embodiments, the timing information may also be stored in the memory 220.

The input device 240 may receive inputs from the user and includes a keyboard, a mouse, a touch screen and/or other input devices. The output device 250 may communicate data to the user via a monitor, a printer and/or other output devices. The receiver 260 and the transmitter 270 may be utilized for wired and/or wireless communications such as with the communications network 150. In an exemplary embodiment, the MDAS 110 may include a combined transceiver to provide the functionalities of the receiver 260 and transmitter 270.

The communications network 150 may be used to assist in communication between the MDASs 110, 120, 130 and the analysis system 160. According to the exemplary embodiments, the communications network 150 may be a network environment using logical connections to one or more remote computers having processors. The logical connections may include a local area network (LAN) and a wide area network (WAN) that are presented here by way of example and not limitation. Such networking environments are commonplace in office-wide or enterprise-wide computer networks, intranets, and the Internet and may use a wide variety of different communication protocols. Those skilled in the art would appreciate that such network computing environments typically encompass many types of computer systems configurations, including personal computers, hand-held devices, multi-processor systems, microprocessor-based or programmable consumer electronics, network PCs, minicomputers, mainframe computers, and the like. Exemplary embodiments of the invention may also be practiced in distributed computing environments where tasks are performed by local and remote processing devices that are linked (either by hardwired links, wireless links or by a combination of hardwired or wireless links) through a communications network. In a distributed computing environment, program modules may be located in both local and remote memory storage devices.

Figure 3:
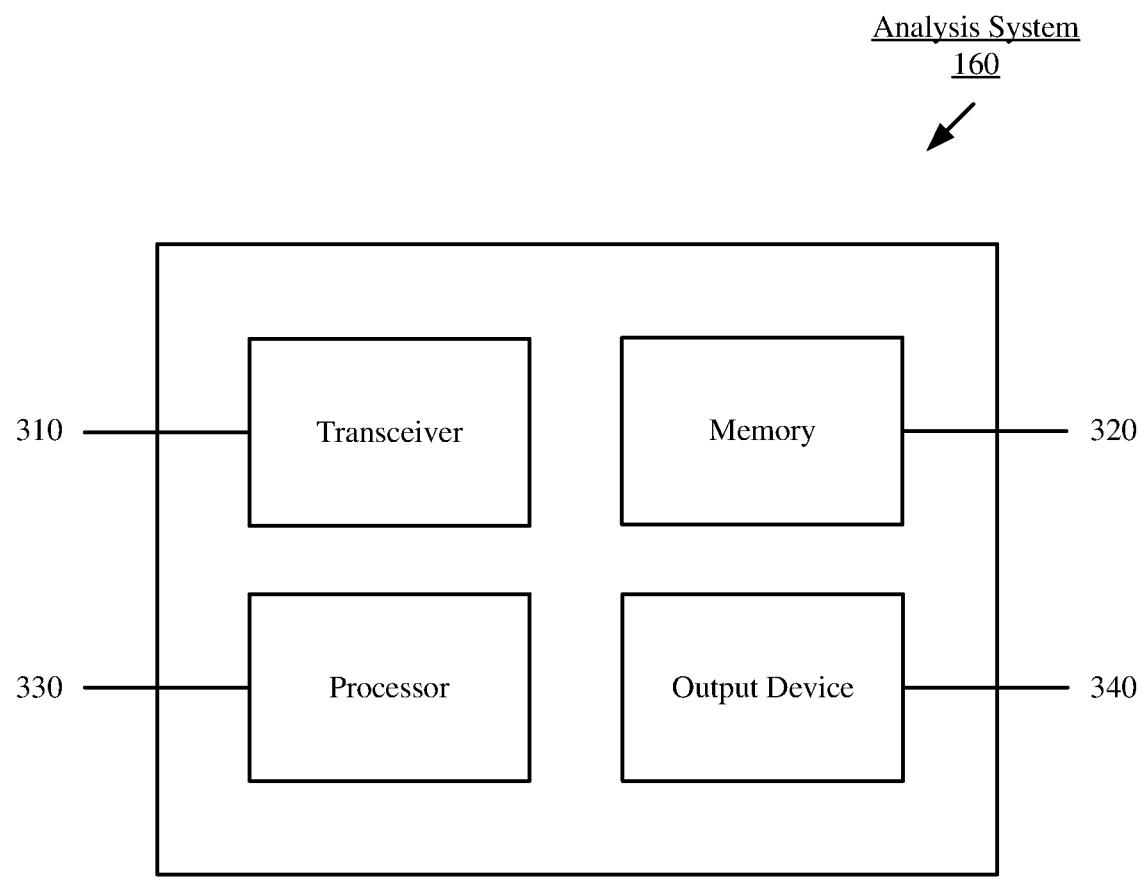
FIG. 3 shows the analysis system of FIG. 1 according to the exemplary embodiments.

The analysis system 160 may be utilized to generate the efficiency data relating to technicians, the schedule for the patients, and the performance data of the MDASs. As will be described in further detail below, the analysis system 160 may receive information from the MDASs 110, 120, 130 via the communications network 150 to determine these types of data. Subsequently, the resulting data may be used to take an appropriate action. FIG. 3 shows the analysis system 160 of FIG. 1 according to exemplary embodiments. The analysis system 160 may include a transceiver 310, a memory 320, a processor 330, and an output device 340. As discussed above, the analysis system 160 may be configured to communicate with the MDASs 110, 120, 130 via the communications network 150.

The processor 310 may utilize the transceiver 310 to communicate with the MDASs 110, 120, 130. The memory 320 may store data received from the MDASs 110, 120, 130 as well as other data and programs necessary to operate the analysis system 160. As will be described in further detail below, the processor 310 may execute at least one of a technician efficiency application, a scheduling application, and a MDAS performance application, all of which may be stored in the memory 320. The memory 320 may also store received data from a plurality of third parties. In further features of the exemplary embodiments, the processor 310 may determine the MDAP and may provide recommendations and/or provide control functions for the MDAS 110, 120, 130 based on the MDAP. The output 340 may output the results from executing the various applications on a monitor, a printer and/or other output devices.

It should be noted that the representation shown in FIG. 3 for the analysis system 160 is only exemplary. Specifically, the analysis system 160 may be embodied in a variety of different configurations such as within a single device (e.g., a server in a network), as a plurality of interconnected devices, as a distributed set of devices, etc. where the configurations may also include cloud based features or virtual forms of the components. For example, the processor 330 may be a cloud based processing engine that performs the functionalities described herein. In another example, the memory 320 may represent one or more data repositories distributed throughout the health care service system 100 such as associated with each of the MDAS 110, 120, 130. In a further example, the analysis system 160 may be embodied as a virtual server that performs the above identified operations. Those skilled in the art will understand that the analysis system 160 may include various other components and features such as a data center in which a processor extracts and transfers data, a multi-node data center, an analytics application with a back-end interacting with the data in the data center and a front-end providing a web user interface, etc.

The exemplary embodiments relate to analytics applications in a radiology environment which has access to various information systems and feeds that contain information about events such as an overall time information. That is, the overall time information may indicate when a MDAP begins and ends. The exemplary embodiments further utilize an extraction of more granular timing information associated with events during the MDAP through joining DICOM metadata with data from the HL7 feed. The granular timing information in the DICOM metadata may provide improved insight into the MDAP workflow and be used to evaluate the technician efficiency, the scheduling, and the MDAS performance. The exemplary embodiments may also be configured to provide interactive data visualization and filtering capabilities to focus on the technician efficiency.

The DICOM metadata in combination with clinical data repository information may provide the more granular information about events during the MDAP, particularly regarding timing information. For example, information about each acquisition may be determined based upon the DICOM metadata. The exemplary embodiments extract the DICOM metadata and join it with the information in the clinical data repository based on the unique study identifier generate by the MDAS 110, 120, 130. From the joined dataset, the exemplary embodiments may obtain information describing specific phases of the MDAP. Specifically, the exemplary embodiments may divide the MDAP into a plurality of intervals including a preparation time, a performance time, a verification time, a contrast time, and a reconstruction time.

The preparation time interval may relate to a time from a start of a MDAP to a first acquisition. The performance time interval may relate to a time from the first acquisition to the last acquisition such as with capturing images. The verification time may relate to a time from the last acquisition to the end of the MDAP. The contrast time interval may relate to a time between two acquisitions between which contrast may be administered. The reconstruction time interval may relate to a total time for all reconstructions performed on the acquired image data. Accordingly, the granular time intervals may provide better insight into the MDAP workflow, technician efficiency, MDAS performance, and may enable subsequent processing to be performed such as determining a schedule.

The exemplary embodiments utilize timestamp information that has been generated during a MDAP to define the distinct exam phases discussed above. The timestamp information may be captured from both the HL7 feed and the DICOM metadata and joining the two data source based on a unique study identifier generated by the MDAS. The following provides a manner in which the analysis system 160 is capable of determining the different intervals corresponding to the various substeps of the MDAP. Specifically, the graphs discussed below may be for one exam in which the x-axis represents time and the y-axis represents a type of timestamp. It is noted that "clinical" refers to timestamps from the HL7 feed which also indicates a start and end of the MDAP. The other timestamps have been extracted from the DICOM metadata and are labeled as "study," "series," "acquisition," "instance creation," and "content" and indicate events occurring during the MDAP. The study timestamp may relate to a time that a study is started; the series timestamp may relate to a time a series is started; the acquisition timestamp may relate to a time a data acquisition is started where an acquisition duration may relate to a duration of a data acquisition; the instance creation timestamp may relate to a time a service-object pair (SOP) (e.g., a DICOM SOP) instance is created; and the content timestamp may relate to a time that an image pixel data creation is started which may be involved in a determination of a reconstruction time.

Figure 4A:
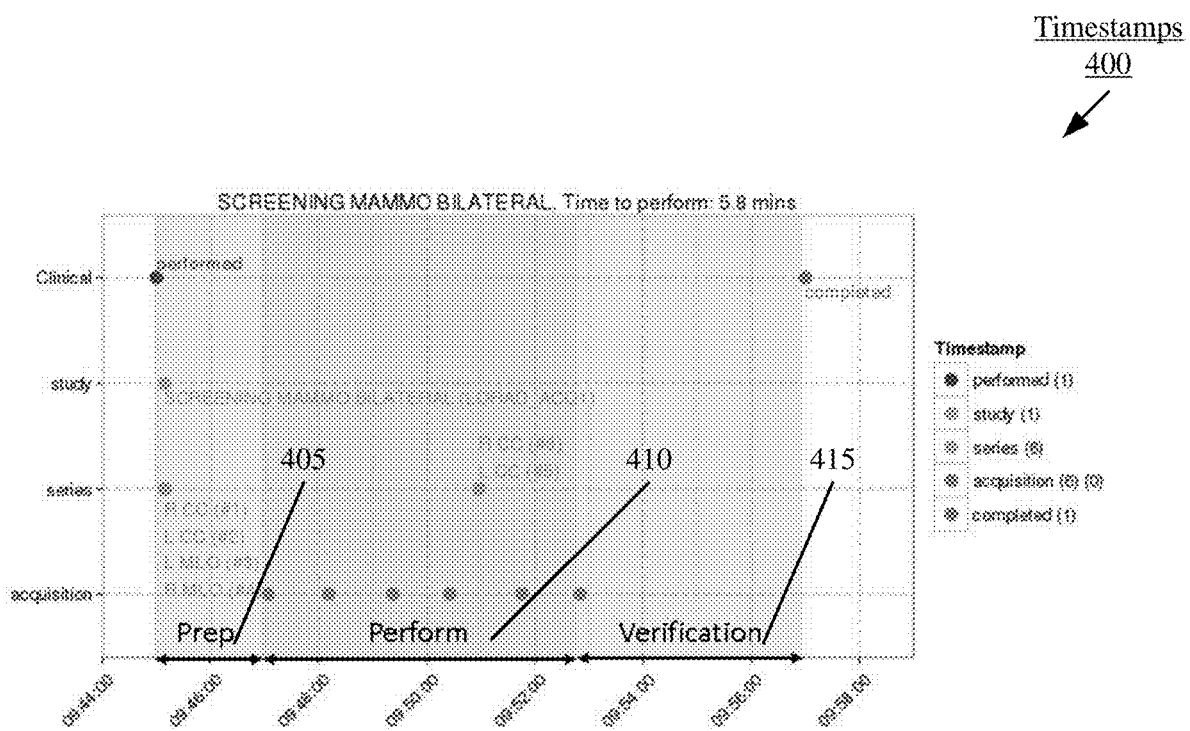
FIG. 4A shows timestamps for a first procedure used as a basis in determining timing information according to the exemplary embodiments.

FIG. 4A shows timestamps 400 for a first procedure used as a basis in determining timing information according to the exemplary embodiments. As illustrated, the DICOM metadata and the HL7 feed may be used as a basis to determine various intervals during the MDAP. With the timestamps 400, the analysis system 160 may determine the preparation interval 405, the performance interval 410, and the verification interval 415. As discussed above, the preparation interval 405 is named based on an assumption that the technician performs preparatory activities in this phase (e.g. positioning the patient or selecting protocols) and may be defined as the time from the start of the MDAP (e.g., approximately 09:45:00) to the first acquisition (e.g., approximately 09:47:00). The performance interval 410 is named based on an assumption that the image acquisition is performed by the technician in this phase and may be defined as the time from the first acquisition (e.g., approximately 09:47:00) to the last acquisition (e.g., approximately 09:53:00). The verification interval 415 is named based on an assumption that the technician performs verification activities in this phase (e.g., examining images for artifacts) and may be defined as the time from the last acquisition (09:53:00) to the end of the MDAP (e.g., approximately 09:57:00). It is noted that the assumptions are in turn based on conversations with clinical experts.

Figure 4B:
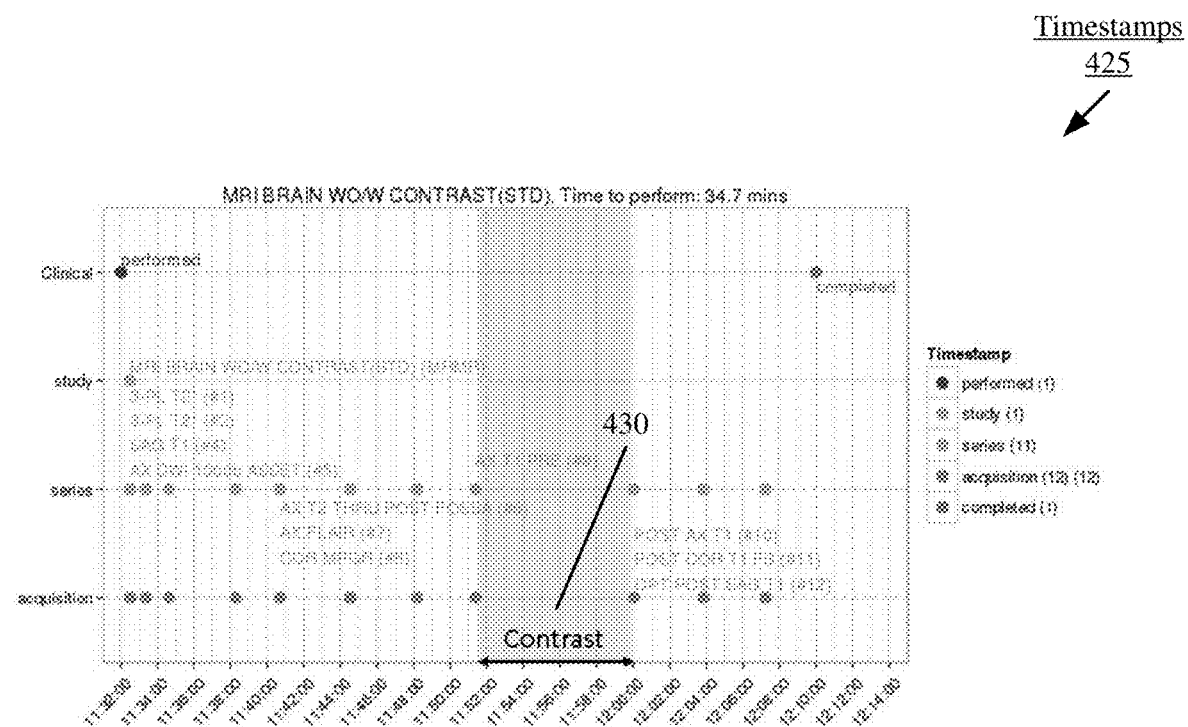
FIG. 4B shows timestamps for a second procedure used as a basis in determining timing information according to the exemplary embodiments.

FIG. 4B shows timestamps 425 for a second procedure used as a basis in determining timing information according to the exemplary embodiments. With the timestamps 425, the analysis system 160 may determine the contrast interval 430. It should be noted that for ease of explanation, the preparation interval, the performance interval, the verification interval, and the reconstruction interval are not shown with the timestamps 425 but may also be determined. As discussed above, the contrast interval 430 may be defined as the time between two acquisitions between which contrast may have been administrated (e.g., approximately from 11:52:00 to 12:00:00) which may be inferred based upon a series description and protocol name associated with the acquisition timestamps such as a series description for an earlier acquisition containing the word "PRE" and for the later acquisition including the word "POST". It is noted that the above manner of inferring that contrast was administered is only exemplary. Those skilled in the art will understand that there are many different manners of performing this operation with various types of information that is used and various inferences or determinations being used in determining the when contrast is administered.

Figure 4C:
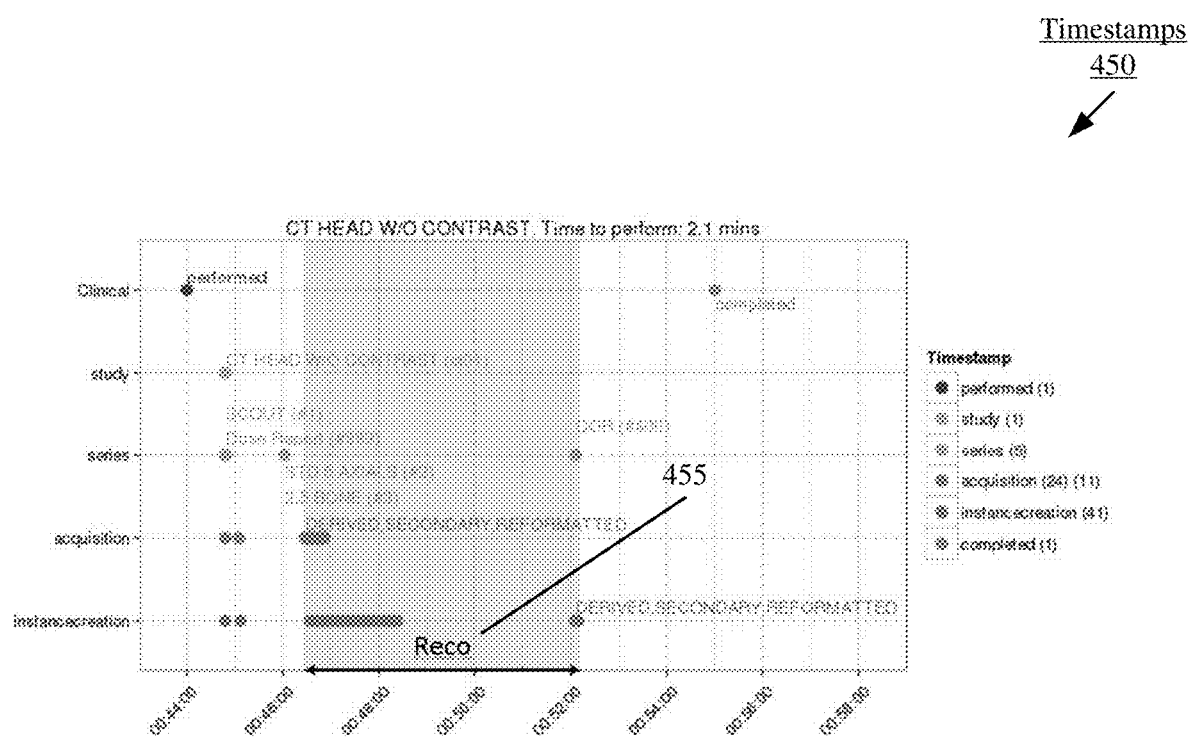
FIG. 4C shows timestamps for a third procedure used as a basis in determining timing information according to the exemplary embodiments.

FIG. 4C shows timestamps 450 for a third procedure used as a basis in determining timing information according to the exemplary embodiments. With the timestamps 450, the analysis system 160 may determine the reconstruction interval 455. As discussed above, the reconstruction interval 455 may be defined as the time between the first acquisition timestamp with the image type "DERIVED" (e.g., approximately 00:46:00) and the last instance creation timestamp with the identical image type (e.g., approximately 00:52:00). It is noted that the above manner of inferring reconstruction time is only exemplary. Those skilled in the art will understand that there are many different manners of performing this operation with various types of information that is used and various inferences and determinations being used in inferring the reconstructions interval. By this definition, the reconstruction interval 455 may encompass all reconstructions being performed.

It should be noted that the above described manner of utilizing the DICOM metadata to extract timing data is only exemplary. That is, the timestamp and time axes are only exemplary. As will be discussed in further detail below, the timing data may be used in a variety of different ways with graphs being generated in different manners as well.

According to a first exemplary embodiment, the analysis system 160 may determine technician efficiency. Specifically, the exemplary embodiments provide a user interface that shows MDAP volume and granular MDAP time intervals for each technician utilizing the MDASs 110, 120, 130. The user interface may enable real-time multivariate interactions with the data.

Figure 5A:
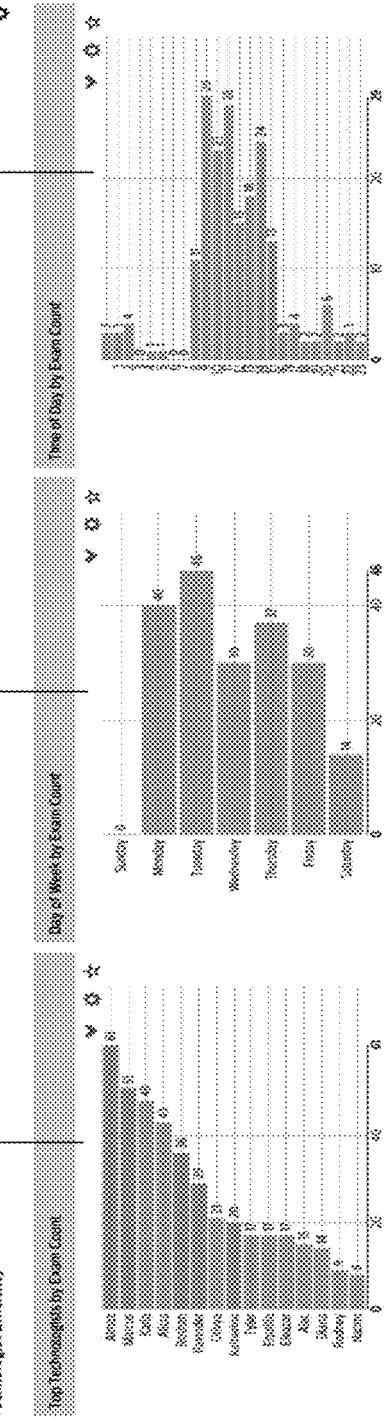
FIG. 5A shows technician efficiency information according to the exemplary embodiments.
Figure 5A:
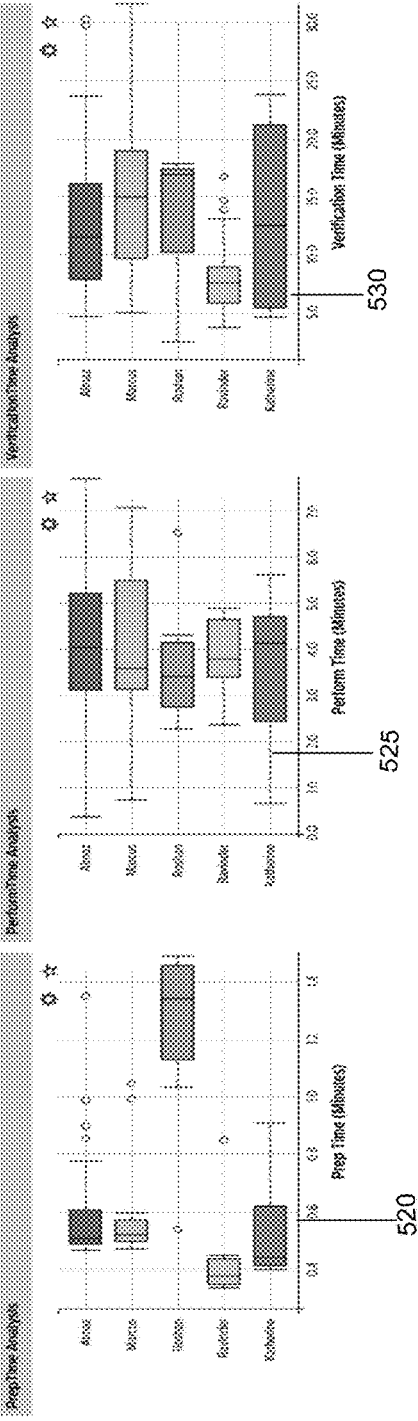

FIG. 5A shows technician efficiency information 500 according to the exemplary embodiments. Specifically, the technician efficiency information 500 may illustrate an exemplary user interface for the relevant information. As shown, the charts 505, 510, 515 show MDAP counts by technician, day of week, and hour of day. The charts 520, 525, 530 show preparation time, performance time, and verification time for selected technicians, days of the week, and hours of the day. The line in each box within the charts 520, 525, 530 may represent a median value. Any selection made in the charts 505, 510, 515 updates all other charts. By providing such a user interface, a reviewer of the results may compare technician efficiency in terms of exam volume and performance times as well as view typical work hours.

Figure 5B:
FIG. 5B shows timeline information for technicians according to the exemplary embodiments.
Figure 5B:
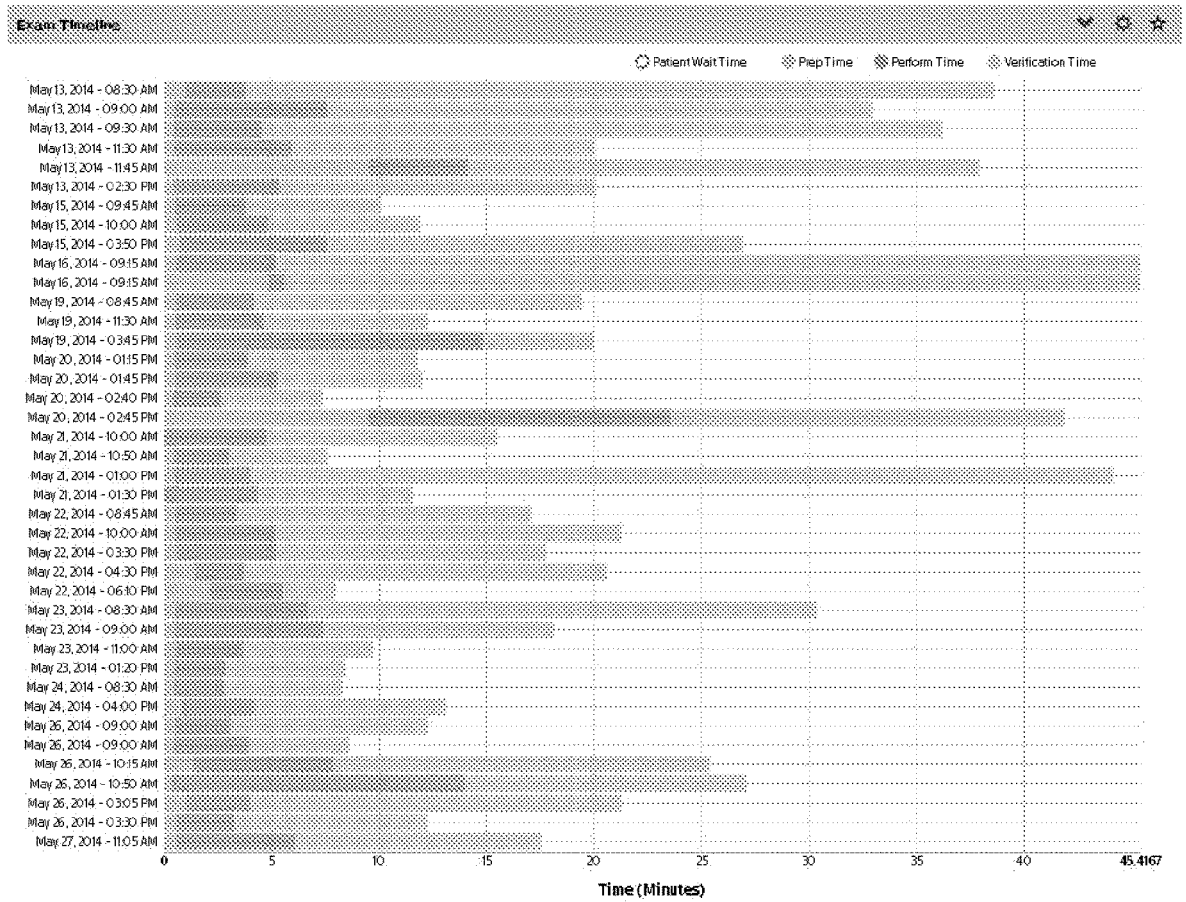

The user interface may also show a view of individual MDAP time lines. FIG. 5B shows timeline information 550 for technicians according to the exemplary embodiments. By hovering over a time line, detailed MDAP information may be shown including the technician and an identity of the MDAS that was used. This view may provide further insight into MDAP workflow and enables for inspecting individual MDAPs when investigating outliers or troubleshooting.

Figure 6:
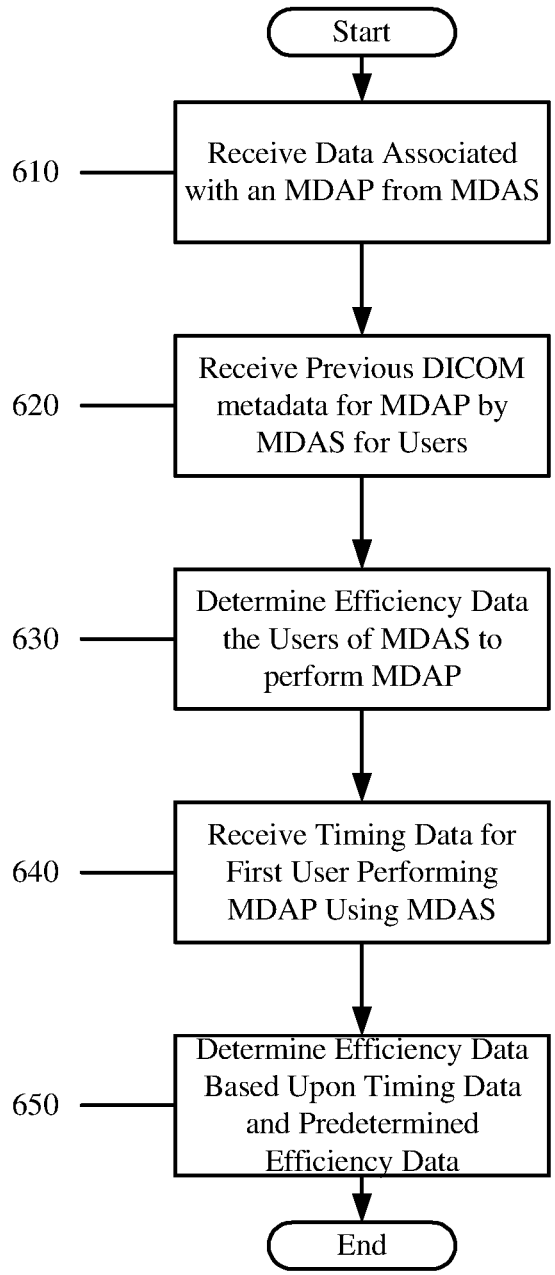
FIG. 6 shows a method of determining technician efficiency according to the exemplary embodiments.

FIG. 6 shows a method 600 of determining technician efficiency according to the exemplary embodiments. The method 600 may incorporate the above described DICOM metadata including timing information when combined with the HL7 feed to determine how a technician performs a MDAP using the MDASs 110, 120, 130.

In step 610, the analysis system 160 may receive data associated with the MDAP from the MDAS. As discussed above, the analysis system 160 may be communicatively connected to the MDASs 110, 120, 130. Thus, upon the MDAP being performed by the technician, the information may be transmitted accordingly. Specifically, the type of MDAP being performed and the identity of the MDAS may be transmitted. In step 620, the analysis system 160 may receive previous DICOM metadata for the MDAP performed by technicians using the identified MDAS of step 610. As discussed above, the timing information therefrom may be extracted and used, particularly as a basis for comparison. In step 630, the analysis system 160 may determine efficiency data of the technicians who have performed the MDAP using the MDAS. In step 640, the analysis system 160 may receive timing data for the current technician performing the MDAP using the identified MDAS. Thus, in step 650, a comparison may be performed where the analysis system 160 determines efficiency data of the technician based upon the timing data and predetermined efficiency data.

It is noted that the method 600 relating to a particular exemplary embodiment in which an efficiency of a specific user to a predetermined efficiency that may be related to one or more users performing the MDAP (specifically with the MDAS) is only exemplary. Those skilled in the art will understand that the efficiency determination may be performed for various other permutations and may be performed using a more granular approach. For example, an efficiency data of a first user may be determined and an efficiency data of a second user may be determined in which the efficiency comparison therebetween may be determined. In another example, efficiency data may be determined for a plurality of users and an efficiency comparison between each of the users may be determined.

By being able to view such information, the reviewer such as an administrator of a hospital that has the MDASs 110, 120, 130 may be capable of performing subsequent actions. Specifically, the administrator may be aware of individual performance rates and the comparison may indicate how a selected technician performs when compared to the other technicians. For example, a best practice routine describing how to perform a procedure may be established based on the procedure adopted by a well-performing technician. In another example, systematic issues may be identified by talking to a poorly-performing technician.

Furthermore, in a further feature of the exemplary embodiment, the analysis system 160 may be configured to automatically determine the actions to be performed. In a particular example of when a first technician is performing sub-optimally and a second technician is performing optimally, the process used by the second technician to perform the MDAP may be recorded. Thus, when the first technician is identified as performing the MDAP, the analysis system 160 may provide the process used by the second technician to improve the performance of the first technician. The analysis system 160 may provide a more passive approach and provide a recommendation to the first technician of the process used by the second technician. The analysis system 160 may provide further automatic processes that utilize the above described information that is generated as a result of the method 600.

According to a second exemplary embodiment, the analysis system 160 may determine a schedule in which patients are to have a respective MDAP performed using a selected MDAS. Specifically, the exemplary embodiments provide an evaluation of technicians performing the different types of MDAPs by using the different MDASs to determine a most efficient manner of utilizing the MDASs by the technicians for a group of patients scheduled for the procedures. That is, observed MDAP times may be used to optimize the time allocation when scheduling.

Figure 7A:
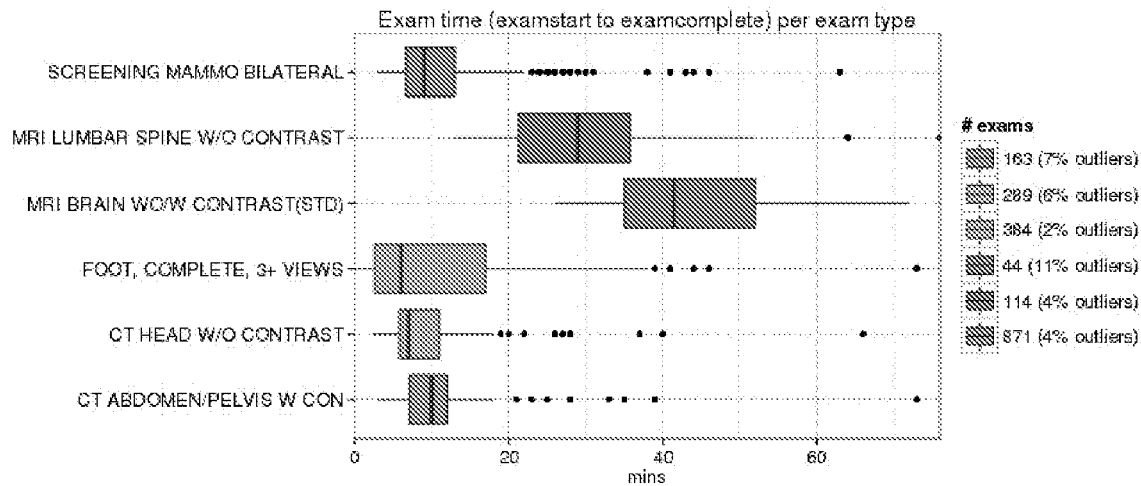
FIG. 7A shows procedure timing information according to the exemplary embodiments.

FIG. 7A shows procedure timing information 700 according to the exemplary embodiments. As shown, the procedure timing information 700 may include information relating to a MDAP (y-axis) relative to time (x-axis). More specifically, each box for the MDAPs may represent an amount of time needed to complete the MDAP (i.e., exam start to exam end). The bar in each box may again represent a median value. The dots along the lines may represent outlier values that may have been ignored for determining the relevant information.

Figure 7B:
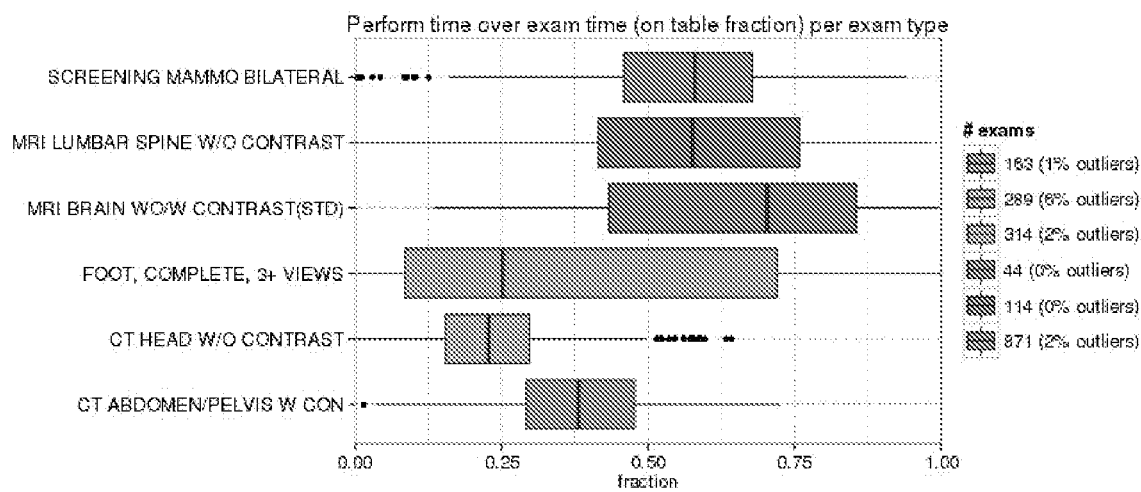
FIG. 7B shows procedure table fraction timing information according to the exemplary embodiments.

FIG. 7B shows procedure table fraction timing information 750 according to the exemplary embodiments. As shown the procedure table fraction timing information 750 may include information relating to a MDAP (y-axis) relative to time (x-axis). More specifically, each box for the MDAPs may represent an amount of time in which the patient had the MDAP performed or an "on table" fraction. Again, the bar in each box may represent a median value whereas the dots along the lines may represent outlier values. As those skilled in the art will understand, the "on table" fraction is a parameter that should be maximized to improve an overall efficiency of use of the MDASs to perform the MDAPs by the technicians. That is, the "on table" fraction may represent a perform time in which the MDAS is being fully utilized. However, the overall MDAP time as shown in FIG. 7A is also an important parameter, particularly when determining a schedule for future patients.

Figure 8:
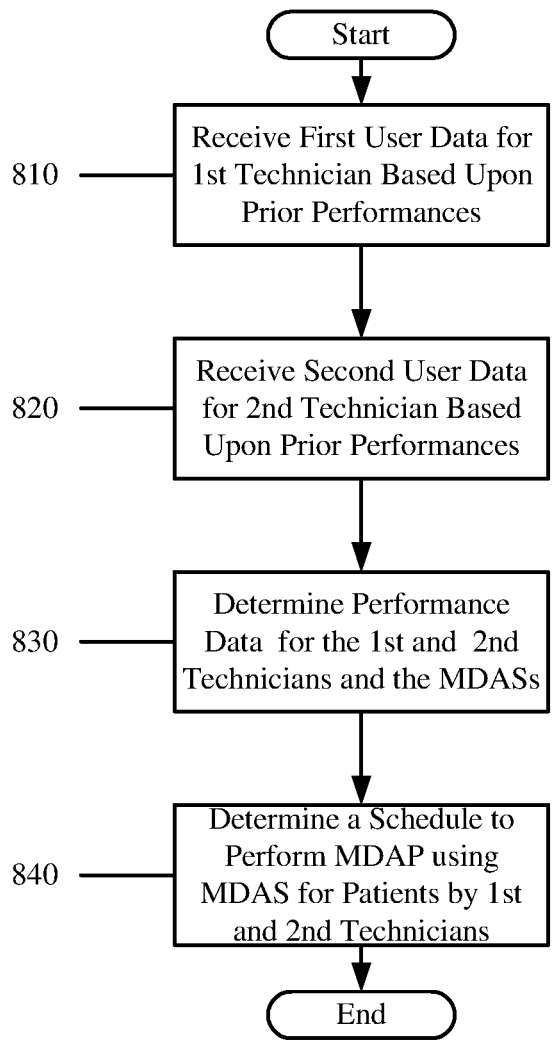
FIG. 8 shows a method of determining a procedure schedule according to the exemplary embodiments.

FIG. 8 shows a method 800 of determining a procedure schedule according to the exemplary embodiments. The method 800 may incorporate the above described DICOM metadata including timing information when combined with the HL7 feed to determine a most efficient way of scheduling patients having respective MDAPs performed by a technician using a respective MDAS 110, 120, 130.

In step 810, the analysis system 160 may receive first user data for a first technician based upon prior performances of various MDAPs using the different MDASs 110, 120, 130. In step 820, the analysis system 160 may receive at least one second user data for a respective second technician based upon prior performances of various MDAPs using the different MDASs 110, 120, 130. In step 830, the analysis system 160 may determine performance data for the technicians and the MDASs 110, 120, 130. For example, the charts shown in FIGS. 7A-B may be generated and shown to an administrator responsible for scheduling MDAPs for patients. Thus, in step 840, the analysis system 160 may determine a schedule to perform the different MDAPs for the patients using the available MDASs 110, 120, 130 by the technicians.

It should be noted that the method 800 is described above with regard to first and second technicians and a scheduling based upon the respective individual performance data. However, this is only exemplary. The method 800 may also be utilized with various modifications. For example, the analysis system 160 may receive user data for a plurality of technicians based upon prior performances and determine an overall performance parameter (e.g., an overall time to spend performing a MDAP). Based upon this performance parameter, the analysis system 160 may determine a schedule to perform the MDPAP using the MDAS for patients by technicians. In a further example, the analysis system 160 may incorporate the information of the individual technicians into the overall performance parameter to refine the overall performance parameter. Accordingly, the scheduling of the technicians may be tailored for the technicians but still based upon the overall performance parameter.

By being able to view such information, the reviewer such as the administrator of the hospital that has the MDASs 110, 120, 130 may be capable of determining a schedule designed for the use of the MDASs to perform the MDAPs based upon an expected time duration for the respective MDAPs to be performed by the technicians. For example, as shown in the charts of FIGS. 7A-7B, an MRI of a brain may require a median time that is highest among the MDAPs while a CT of a head without contrast requires a median time that is lowest among the MDAPs. The timing data may also be correlated to the technician who performed the MDAP. With such knowledge and given a set of scheduled MDAPs that are to be performed in a given day or time period, the analysis system 160 may generate a schedule to most effectively utilize the technicians to perform a variety of different MDAPs using the MDASs 110, 120, 130. That is, the analysis system 160 may further receive inputs for future MDAPs and automatically generate the schedule accordingly.

According to a third exemplary embodiment, the analysis system 160 may determine MDAS utilization and performance. Specifically, the exemplary embodiments may utilize the granular MDAP times extracted from the DICOM metadata as a basis for comparison between the different MDASs 110, 120, 130 for a common MDAP type. This may be indicative of significant variations in efficiency that may be attributed to the MDAS instead of the technicians. Specifically, the reconstruction time may specifically apply directly to the MDAS.

Figure 9:
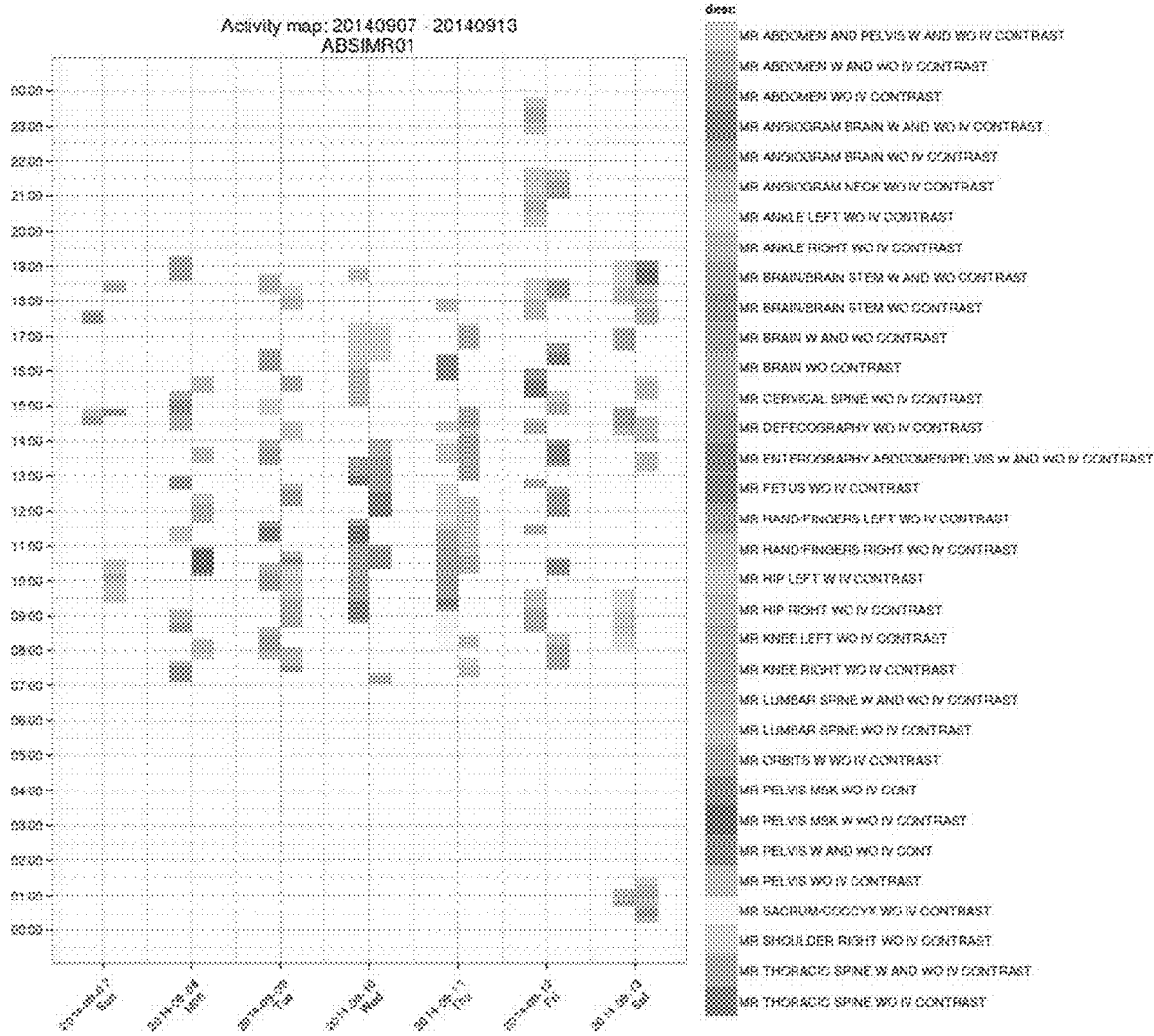
FIG. 9 shows an activity map for device utilization according to the exemplary embodiments.

FIG. 9 shows an activity map 900 for device utilization according to the exemplary embodiments. The analysis system 160 may generate the activity map 900 that details an overview of the utilization of the MDASs 110, 120, 130. For example, the activity map 900 shows activity of a single MDAS over a period of a week. The time of day may be represented on the y-axis whereas the day of the week may be represented on the x-axis. Each box may represent a single exam where a darker region of the box is a performance time and the lighter region of the box is before the preparation time and after the verification time. Using a color coding scheme or shading, the type of MDAP may also be represented. The activity map 900 may provide a quick overview of the activity of the MDAS since the white area (i.e., empty space) represents an idle time which may be extracted and viewed as a function of time or compared between, for example, MDASs, locations, modality types, etc. to identify the inefficiencies or issues that may exist with the MDASs 110, 120, 130.

Figure 10:
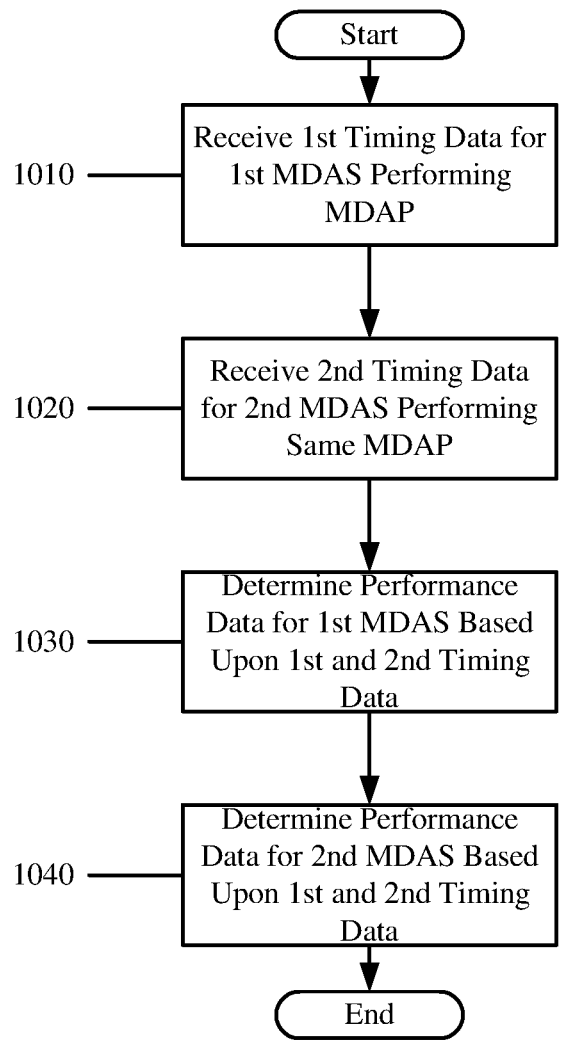
FIG. 10 shows a method of determining performance information of devices according to the exemplary embodiments.

FIG. 10 shows a method 1000 of determining performance information of devices according to the exemplary embodiments. The method 1000 may incorporate the above described DICOM metadata including timing information when combined with the HL7 feed to determine an efficiency or potential issues that may be present with the MDASs 110, 120, 130.

In step 1010, the analysis system 160 may receive first timing data for a first MDAS performing a given MDAP. In step 1020, the analysis system 160 may receive second timing data for a second MDAS performing the same MDAP. In step 1030, the analysis system 160 may determine performance data for the first MDAS based upon the first and second timing data. In step 1040, the analysis system 160 may determine performance data for the second MDAS based upon the first and second timing data. Specifically, the performance data of the first and second MDASs may be a comparison of an overall efficiency based upon both the MDASs. Thus, with a constant MDAP being performed (more particularly by a common technician who assumedly performs the MDAP in an identical manner), a comparison between the performance of the MDAS may be evaluated.

By being able to view such information, the reviewer such as the administrator of the hospital that has the MDASs 110, 120, 130 may be capable of determining an efficiency of the MDASs 110, 120, 130. This information may enable the reviewer to address inefficient utilization of the MDASs 110, 120, 130. For example, if one MDAS is idle for a significant amount of time while another MDAS is always fully utilized, the reviewer may redistribute the load or select to take on more patients. In another example, if all of the MDASs 110, 120, 130 are fully utilized, the reviewer may be motivated to consider the acquisition of a further MDAS. In a further example, the reviewer may determine whether the MDASs 110, 120, 130 have any issues such as maintenance issues or workflow issues related to ergonomics using this information.

Furthermore, as described above, a feature that may be incorporated is the analysis system 160 being incorporated into the workflow. That is, the analysis system 160 may be configured to automatically determine the actions to be performed. It should be noted that the incorporation of the analysis system 160 into the workflow is only exemplary and the analysis system 160 may remain outside the workflow to provide data or recommendations without direct intervention. In a particular example, the results of the above generated information may indicate when one of the MDASs 110, 120, 130 is operating at a level under a predetermined threshold. The predetermined threshold may indicate that the MDAS has an issue (e.g., broken component, update required, etc.). If a technician attempts to use the MDAS at issue, the analysis system 160 may automatically perform a variety of actions such as providing an alert that an administrator should be notified, providing an alert that the MDAS has an issue, etc. The analysis system 160 may provide further automatic processes that utilize the above described information that is generated as a result of the method 600.

It should be noted that the activity map 900 shows a plurality of different MDAPs. The analysis may relate to a single MDAP to filter the analysis of the MDAS. However, those skilled in the art will understand that different MDAPs may utilize common procedure substeps. The information provided in the activity map 900 may also provide information regarding these common substeps to further narrow the type of issue that may exist on the MDAS.

It should also be noted that the activity map 900 is based upon the MDASs. However, this is only exemplary. In another example, the activity map 900 may also be generated for the technicians to get an overview of their activity as well in a manner similar to the MDAS efficiency evaluation discussed above. For example, when a technician is analyzed, it would be obvious from the activity map if the technician systematically completed MDAPs in the RIS at the end of the day instead of directly following the MDAP.

According to the exemplary embodiments, the system and method of the exemplary embodiments provide an analysis mechanism to determine technician efficiency, to determine a schedule to most effectively utilize the technicians and MDASs, and to determine performance data of MDASs. Specifically, DICOM metadata may be combined with information of the HL7 feed to extract granular timing information that gives improved insight into MDAP workflow, particularly as timing information of the substeps of the MDAP may also be determined instead of relying solely upon an overall timing information of the MDAP.

Those skilled in the art will understand that the above described exemplary embodiments may be implemented in any suitable software or hardware configuration or combination thereof. An exemplary hardware platform for implementing the exemplary embodiments may include, for example, an Intel x86 based platform with compatible operating system, a MAC platform and MAC OS, a mobile hardware device having an operating system such as iOS, Android, etc. In a further example, the exemplary embodiments of the above described method may be embodied as a program containing lines of code stored on a non-transitory computer readable storage medium that, when compiled, may be executed on a processor or microprocessor.

It will be apparent to those skilled in the art that various modifications may be made in the present invention, without departing from the spirit or the scope of the invention. Thus, it is intended that the present invention cover modifications and variations of this invention provided they come within the scope of the appended claims and their equivalent.

What is claimed is:

1. A method for determining efficiency data for a Medical Data Acquisition Procedure (MDAP) performed by at least a first technician using at least a first Magnetic Resonance Imaging (MRI) device, wherein the MDAP comprises generating cross sectional and axial images of internal structures of a body, wherein patients are scheduled for the MDAP performed using the first MRI device, the method comprising:

receiving first Digital Imaging and Communications in Medicine (DICOM) metadata obtained during performance of the MDAP using the MRI device by the first technician, the DICOM metadata including first timestamp information relating to events that occurred during the MDAP;

determining first durations of a plurality of predefined stages of the MDAP on the basis of the first timestamp information, each stage being defined as an interval between predetermined events, wherein the stages include a preparation time interval, a performance time interval, a verification time interval, a contrast time interval, and a reconstruction time interval;

determining first efficiency data of the first technician as a function of the determined durations and predetermined efficiency data defined for the MDAP using the first MRI device;

receiving further DICOM meta data obtained during at least one prior performance of the MDAP using the MRI device by a second technician including second timestamp information relating to events that occurred during the MDAP;

determining second durations of the plurality of predefined stages of the MDAP on the basis of the second timestamp information;

determining second efficiency data of the first technician as a function of the determined durations and predetermined efficiency data defined for the MDAP using the first MRI device;

comparing the first efficiency data of the first technician and the second efficiency data of the second technician; and automatically providing a process for the MDAP performed by the second technician to the first technician based on the comparison of the first efficiency data and the second efficiency data.

2. The method of claim 1, wherein the predetermined efficiency data is generated based upon previously received DICOM metadata associated with performing the MDAP using the first MRI device by the first technician and at least one further technician.

3. The method of claim 1, wherein the first and second timestamp information is extracted from the DICOM metadata to determine durations of each of the stages of the MDAP.

4. The method of claim 1, wherein the pre pa ration time interval is defined from a start of the MDAP to a start of a first acquisition, the performance time interval is defined from a start of the first acquisition to an end of a last acquisition, the verification time interval is defined from the end of the last acquisition to an end of the MDAP, the contrast time interval is defined as a time between two acquisitions between which contrast was administered, and the reconstruction time interval is defined from a first acquisition timestamp to a last instance creation.

5. The method of claim 2, further comprising:
receiving an input indicating a type of the MDAP performed by the first MRI device; and
filtering the previously DICOM metadata for the indicated MDAP.

6. The method of claim 1, further comprising:
determining additional performance data for the first MRI device and at least one further MRI device as a function of the first performance data, the further DICOM meta data, the type of the MRI device, a type of the further MRI device and the type of the MDAP.

7. The method of claim 1, further comprising:
determining second performance data for the first technician based on an on-table fraction
indicating a time period when the first MRI device is being utilized to perform the MDAP.

8. The method of claim 1, wherein performance data of a plurality of MRI device performing the Medical MDAP are determined and wherein the method further comprises:
receiving second DICOM metadata obtained during the MDAP by a second M RI device, the second DICOM metadata including timestamp information relating to events that occurred during the MDAP using the second MRI device; and
determining the performance data for each of the first and second MRI device based upon the first and second DICOM metadata.

9. The method of claim 8, wherein the first and second DICOM metadata are associated with a common technician performing the MDAP using the first MRI device and the second MRI device.

10. The method of claim 8, further comprising:
generating an activity map showing the MDAP performed by the first MRI device and the second MRI device relative to a time period.

11. The method of claim 1, further comprising:
determining first performance data for the first technician as a function of the first durations.

12. The method of claim 11, further comprising:
determining second performance data for the first technician as a function of the second durations.

13. The method of claim 12, further comprising:
automatically generating a schedule for the patients to have the MDAP performed using the first MRI device based on at least the first and second performance data.

14. The method of claim 1, further comprising:
providing recommendations for a type of MRI device based on the MDAP, wherein the recommendations comprise an alert for the type of MRI device that is inefficient.

15. The method of claim 1, further comprising:
generating control functions for a type of MRI device based on the MDAP.

\* \* \* \* \*